(12) United States Patent
Raju et al.

(10) Patent No.: US 10,034,658 B2
(45) Date of Patent: Jul. 31, 2018

(54) CONSISTENT SEQUENTIAL ULTRASOUND ACQUISITIONS FOR INTRA-CRANIAL MONITORING

(71) Applicant: KONINKLIJKE PHILIPS N.V., Eindhoven (NL)

(72) Inventors: Balasundar Iyyavu Raju, Chester, NY (US); William Tao Shi, Briarcliff Manor, NY (US); Francois Guy Gerard Marie Vignon, Croton on Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 225 days.

(21) Appl. No.: 14/769,218

(22) PCT Filed: Feb. 25, 2014

(86) PCT No.: PCT/IB2014/059232
§ 371 (c)(1),
(2) Date: Aug. 20, 2015

(87) PCT Pub. No.: WO2014/136016
PCT Pub. Date: Sep. 12, 2014

(65) Prior Publication Data
US 2016/0000411 A1    Jan. 7, 2016

Related U.S. Application Data

(60) Provisional application No. 61/772,717, filed on Mar. 5, 2013.

(51) Int. Cl.
*A61B 8/00* (2006.01)
*A61B 5/00* (2006.01)
(Continued)

(52) U.S. Cl.
CPC .............. *A61B 8/54* (2013.01); *A61B 5/6842* (2013.01); *A61B 8/0808* (2013.01); *A61B 8/14* (2013.01);
(Continued)

(58) Field of Classification Search
CPC ....... A61B 8/54; A61B 8/0808; A61B 8/4245; A61B 8/46; A61B 8/5223; A61B 8/14;
(Continued)

(56) References Cited

U.S. PATENT DOCUMENTS 4,390,025 A * 6/1983 Takemura ................ A61B 8/14
348/163
5,226,419 A   7/1993 Hanrahan
(Continued)

FOREIGN PATENT DOCUMENTS

EP       1525850 A1    4/2005

OTHER PUBLICATIONS

Nightingale, Kathryn R. et al "The Use of Acoustic Streaming in Breast Lesion Diagnosis: A Clinical Study", Ultrasound in Medicine and Biology, vol. 25, No. 1, 1999, pp. 75-87.
(Continued)

*Primary Examiner* — Jennifer Dieterle
*Assistant Examiner* — Angela M Hoffa

(57) ABSTRACT

A medical imaging probe (102) for contact with an imaging subject includes an indicium placement apparatus for, while the probe is in contact, selectively performing an instance of marking the subject so as to record a position of the probe. The device may further include a feedback module for determining whether an orientation, with respect to a the mark, that currently exists for a medical imaging probe of the device meets a criterion of proximity to a predetermined orientation. Responsive to the determination that the criterion is met, a quantitative evaluation may be made auto-
(Continued)

matically and without need for user intervention, via live imaging via the probe, of a lesion that was, prior to the determination, specifically identified for the evaluation. Change, such as growth (116), in the lesion, like a brain lesion, may thereby be tracked over consistent sequential imaging acquisitions, such as through ultrasound.

13 Claims, 5 Drawing Sheets

(51) Int. Cl.
*A61B 8/08* (2006.01)
*A61B 8/14* (2006.01)
*A61B 90/00* (2016.01)

(52) U.S. Cl.
CPC .............. *A61B 8/42* (2013.01); *A61B 8/4245* (2013.01); *A61B 8/46* (2013.01); *A61B 8/5223* (2013.01); *A61B 2090/395* (2016.02)

(58) Field of Classification Search
CPC .... A61B 5/6842; A61B 8/42; A61B 2090/395
See application file for complete search history.

(56) References Cited

U.S. PATENT DOCUMENTS

| | | | |
|---|---|---|---|
| 5,487,387 A | 1/1996 | Trahey | |
| 5,690,113 A | 11/1997 | Sliwa | |
| 5,951,476 A | 9/1999 | Beach | |
| 6,299,579 B1 | 10/2001 | Peterson | |
| 7,806,824 B2* | 10/2010 | Ohtake | A61B 8/00 600/407 |
| 7,892,188 B2 | 2/2011 | Walker | |
| 7,933,007 B2 | 4/2011 | Stanton | |
| 8,060,189 B2 | 11/2011 | Dor | |
| 2002/0103434 A1 | 8/2002 | Swanbom | |
| 2004/0019270 A1* | 1/2004 | Takeuchi | A61B 8/14 600/407 |
| 2005/0085727 A1 | 4/2005 | Swanbom | |
| 2005/0090746 A1* | 4/2005 | Ohtake | A61B 8/08 600/447 |
| 2005/0119569 A1* | 6/2005 | Ohtake | A61B 8/00 600/437 |
| 2006/0106312 A1 | 5/2006 | Farmer | |
| 2009/0043196 A1* | 2/2009 | Sakai | A61B 8/485 600/437 |
| 2009/0177092 A1 | 7/2009 | Riechers | |
| 2010/0004540 A1 | 1/2010 | Thiele | |
| 2010/0194879 A1 | 8/2010 | Pasveer | |
| 2010/0268072 A1* | 10/2010 | Hall | A61N 7/02 600/427 |
| 2011/0028867 A1* | 2/2011 | Choo | A61N 7/02 601/2 |
| 2012/0143058 A1 | 6/2012 | Powers | |
| 2012/0165670 A1* | 6/2012 | Shi | G01S 7/52049 600/442 |
| 2016/0012582 A1* | 1/2016 | Mauldin, Jr. | A61B 8/0875 382/131 |
| 2016/0143627 A1* | 5/2016 | Vignon | G06T 7/74 600/437 |

OTHER PUBLICATIONS

Edwards, A. et al"Acoustic Streaming: A New Technique for Assessing Adnexal Cysts", Ultrasound Obstet Gynecol. vol. 22, 2003, pp. 74-78.

Nightingale, Kathryn R. et al "A Novel Ultrasonic Technique for Differentiating Cysts from Solid Lesions: Preliminary Results in the Breast", Ultrasound in Medicne and Biology, vol. 21, No. 6, 1995, pp. 745-751.

Starritt, H.C. et al "An Experimental Investigation of Streaming inPulsed Diagnostic Ultrasound Beams", Ultrasound in Medicne and Biology, vol. 15, No. 4, 1989, pp. 363-373.

* cited by examiner

CONSISTENT SEQUENTIAL ULTRASOUND ACQUISITIONS FOR INTRA-CRANIAL MONITORING

CROSS-REFERENCE TO PRIOR APPLICATIONS

This application is the U.S. National Phase application under 35 U.S.C. § 371 of International Application No. PCT/IB2014/059232, filed on Feb. 25, 2014, which claims the benefit of U.S. Provisional Patent Application No. 61/772,717, filed on Mar. 5 2013. These applications are hereby incorporated by reference herein.

FIELD OF THE INVENTION

The present invention relates to a position of a medical imaging probe and, more particularly, to the position while the probe is in contact with an imaging subject.

BACKGROUND OF THE INVENTION

According to the Centers for Disease Control and Prevention (CDC), trauma accounts for 42 million emergency department visits and 2 million hospital admissions across the USA every year. In the USA, trauma accounts for 38.4 deaths per 100,000 of population. Trauma is especially a leading cause of death in the young population, and accounts for 30% of all life years lost in the USA (compared to 16% for cancer, and 12% for heart diseases). Head injury in particular counts for 30% of total trauma cases. Trauma is also the $5^{th}$ leading cause of death worldwide.

Ultrasound is often the first imaging examination of patients with major trauma. Ultrasound is non-invasive and portable and is available at low cost compared to computed tomography (CT) or magnetic resonance imaging (MRI).

The FAST (Focused Assessment with Sonography in Trauma) protocols were developed to streamline the process of quick examinations of a trauma patient in the emergency room (ER) by relatively untrained users. The aim of the FAST examination is to assess blood accumulation in four areas in the abdomen/chest, where under normal conditions blood would not be present. For instance in the RUQ examination, the user is examined for dark hypoechogenic areas in the Morrison's pouch, the space between the liver and right kidney, where the hypoechogenicity would indicate presence of accumulated blood.

However there is no equivalent FAST examination to quickly detect and monitor intra-cranial blood. This is most likely due to the need to be able to obtain a good scan and interpret intracranial ultrasound images, both of which require considerable skill.

In addition to trauma events, another cause for intracranial bleeding is intracerebral hemorrhagic stroke, which accounts for 10-15% of all strokes and occurs due to rupture of blood vessels in the brain due to hypertension. In patients suspected of having suffered a stroke event it is necessary to quickly assess whether or not there is bleeding, so that proper drugs can be administered in a timely manner. In addition, hemorrhagic transformation is a natural consequence of ischemic stroke. It is exacerbated by the administration of clot-dissolving medicine such as tPA, and the hemorrhagic transformation can have more devastating effects than the original stroke itself.

In most situations involving head trauma or hemorrhagic stroke, it is necessary to monitor the patient over a period of time. For instance in trauma, it is necessary to monitor whether additional bleeding has occurred as evidenced by changes in the size of the blood pool. Some hemorrhages develop inside areas of ischemia ("hemorrhagic transformation"), which needs monitoring over a period of time.

Currently, a device, described in U.S. Pat. No. 8,060,189 to Dor et al. (hereinafter "the '189 patent"), known as Infrascanner that uses near infra-red light is available to detect peripheral blood in the brain (mostly epidural and subdural hematomas), but the device can work only up to a limited depth of 2.5 centimeters.

SUMMARY OF THE INVENTION

What is proposed herein below is directed to addressing one or more of the above concerns.

While CT can be used for the initial assessment of trauma and stroke victims, repeated CT examinations are not advisable due to the high radiation dose. Also, it is impractical to move the patient from the bed to the CT room for repeated follow-ups. In many centers, a delay of about one hour to performing a CT scan is common.

Thus, having a portable means, such as ultrasound, to make the evaluations repeatedly over a period of time is highly preferred.

Transcranial ultrasound scans, however, are difficult to perform and require considerable expertise. The examination is operator dependent and subjective. When quantitative measurements are used in intra-cranial monitoring such as to detect relative changes over time, the probe placement at various time points would significantly affect the magnitude of the measurements such as lesion size and tissue displacements and would mask any changes that are due to a change in clinical condition. This is because changes in the probe position and/or angle lead to drastically different acoustic windows due to the uneven nature of the skull, leading to different transmit amplitudes and backscattering properties.

Thus, it is necessary to use methods that ensure that probe placement is tracked and adjusted so that nearly similar acoustic propagation windows are used at all the time points.

The device of the '189 patent, in addition to limited depth of imaging, also does not provide a quantitative measurement of the extent of the lesion and does not enable lesion monitoring.

No device presently exists to quickly ascertain presence and monitoring of intra-cranial hemorrhage that can be used in an ER or pre-hospital setting without significant user expertise.

In accordance with an aspect of the present invention, a medical imaging probe, configured for contact with an imaging subject, includes an indicium placement apparatus. The apparatus is configured for, while the probe is in contact with the subject, selectively performing an instance of marking the subject so as to record a position of the probe.

In one sub-aspect, the subject has skin, and the marking is performed to mark the skin.

In another sub-aspect, the marking entails printing with ink.

In a different sub-aspect, a medical imaging device includes the probe, and a user control for triggering the instance of marking.

In a further sub-aspect, the probe includes the user control.

In a first related sub-aspect, the device is further configured for, responsive to the instance of marking and without need for further user intervention, interrogating the imaging subject, via imaging, to evaluate current physical structure in search of a lesion.

In one particular sub-aspect, the device is further configured for emitting ultrasound, receiving ultrasound, or both.

In a related sub-aspect, a medical imaging device includes the probe and further includes a feedback module configured for determining whether an orientation, with respect to a mark resulting from the instance of marking, that currently exists for a medical imaging probe of the device meets a criterion of proximity to a predetermined orientation.

As a further sub-aspect, the predetermined orientation is an orientation, with respect to the mark, that existed, at the time of the marking, for the probe performing the marking.

In another, further sub-aspect, the marking provides a landmark on the imaging subject, and the feedback module, by the determining that the criterion is met, also determines that a current position of the probe matches the landmark.

In one other further sub-aspect, the device is configured for, automatically and without need for user intervention, performing the instance of marking responsive to, via displacement imaging of the imaging subject, detecting a lesion. The device is further configured such that a field of view of the probe whose orientation is subject to the determining will, upon the determining that the criterion is met, include the lesion.

In still another, further sub-aspect, the determining includes pattern matching based on radiofrequency (RF) data currently being acquired via the probe whose orientation is subject to the determining.

In a yet, further sub-aspect of the above, the RF data spans a current field of view within said subject, and the determining entails detecting a region of fluid and excluding the region from the pattern matching.

In an alternative, complementary or more specific further sub-aspect, the criterion is based on proximity of a current pattern of reflection from bone, reverberation from bone, or both reverberation and reflection from bone correspondingly to a reference pattern of reflection from bone, reverberation from bone, or both reverberation and reflection from bone.

As yet another further sub-aspect, the module further features a user indicator configured for providing a real-time indication of closeness in the meeting of the criterion.

In a yet, different further sub-aspect, the criterion is based on mutual proximity of patterns of delay and/or amplitude over transducer elements.

As one other further sub-aspect, the device is configured for, responsive to the determination that the proximity criterion is met and without need for further user intervention, interrogating the imaging subject, via imaging, to evaluate a pre-identified lesion.

In an associated further sub-aspect, the device is configured for, after the determination that the criterion is met, evaluating, via imaging, current size of a specific lesion that was identified prior to said determination, current physical structure of said lesion, or both.

In a yet, further sub-aspect, the device is configured for performing the evaluating responsive to the determination that the criterion is met, and for performing it automatically and without need for user intervention.

As a still further sub-aspect, the automatic action, without the need, further includes comparing the respective evaluated size and/or physical structure correspondingly to a previously-evaluated size and/or physical structure.

In a complementary sub-aspect, a medical imaging device that includes the probe is further configured for, after a lesion of the medical subject has been identified and while a medical imaging probe of the device is applied to the marked position, affording user guidance that interacts with user manipulation of the applied probe. The device is further configured for, automatically and without need for further user intervention, monitoring, via imaging via the applied probe, the lesion specifically and for change in the lesion.

In a still further sub-aspect, the device is further configured specifically for concurrently monitoring normal tissue, and for comparing the change in the lesion to change in the normal tissue.

In an alternative further sub-aspect, the lesion is a brain lesion.

In accordance with a related version, a computer-readable medium embodies instructions executable by a processor for at least:

a) operating a feedback module configured for, via imaging via a medical imaging probe, determining, automatically and without need for user intervention, whether a current orientation of the probe meets a criterion of proximity to a predetermined orientation; and b) responsive to the determination that the criterion is met, making automatically and without need for user intervention, via imaging via the probe, a quantitative evaluation of a lesion that was, prior to the determination, specifically identified for the evaluation.

Details of the novel probe, device and computer-readable medium are set forth further below, with the aid of the following drawings, which are not drawn to scale.

DETAILED DESCRIPTION OF EMBODIMENTS

Figure 1:
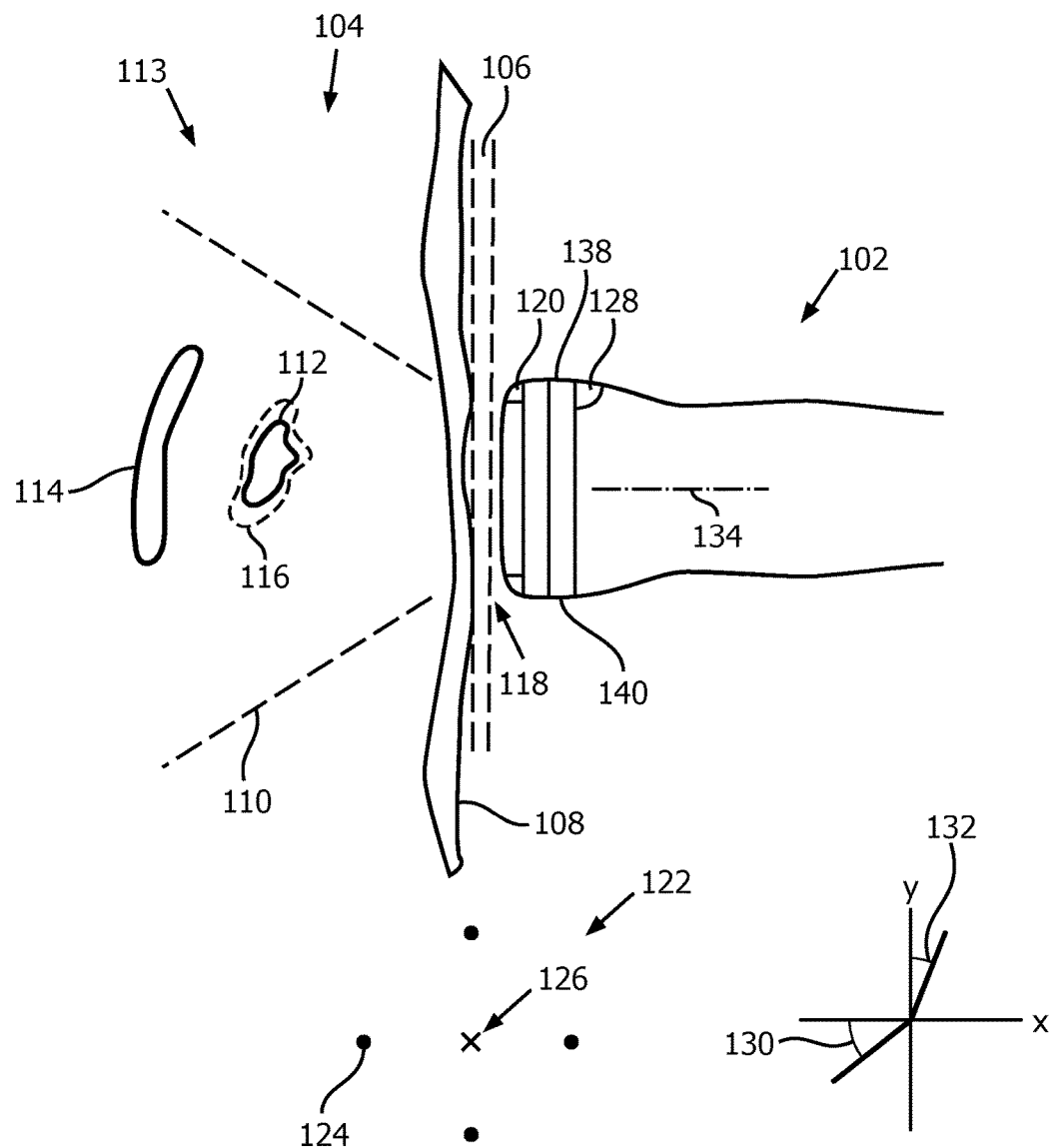
FIG. 1 is a schematic view of a medical imaging device, including a probe, in accordance with the present invention.

FIG. 1 depicts an exemplary probe 102 for consistent sequential ultrasound acquisitions for intra-cranial monitoring of a medical subject 104, such as a human patient or animal.

It will be assumed, in the description that follows, that this single probe 102 is used for all the acquisitions. However, a medical imaging device could feature one or more other probes, any one of which can be applied to the subject 104 for a given acquisition. In this disclosure, any of the probes, if there are more than one, could be characterized as "a probe said medical imaging device comprises." Otherwise, if there is a single probe, that probe is "a probe said medical imaging device comprises."

The probe 102 is applied to skin 106 of the subject 104 in the temple area of the head. The probe 102 is therefore pressed against an underlying, bony structure, a temporal bone 108. Due to the uneven nature of the temporal bone 108, changes in the probe position and/or angle lead to drastically different acoustic windows. The temporal bone 108 therefore provides a signature unique to a particular position and orientation of the probe 102. The probe 102 has a current field of view (FOV) 110 within which reside a lesion 112 of the brain 113 and a selected surrounding or nearby normal region 114. It will be assumed hereinafter that only a single lesion is being monitored, although more than one lesion within a field-of-view could simultaneously be monitored. Growth or other change 116 in the lesion 112 is monitored over sequential ultrasound acquisitions done over a span of time. The change 116, if any, can be normalized against any corresponding change, if any, in the normal region 114. The normal region(s) 114 serve a dual purpose. Besides providing the basis for lesion growth normalization, the normal region(s) 114 are imaged for pattern matching so that the probe orientation can be kept consistent over the separate acquisitions needed to track, over time, growth and/or change 116 in physical structure, i.e., the solid/fluid mix or hardening of a clot. Portions of the normal region(s) 114 utilized for one of the purposes may be different, such as separate or overlapping, from those portions used for the other purpose.

The probe 102 includes, at its head an indicium placement apparatus 118. The apparatus 118 has a number of discharge ports 120 around the periphery of the face of the probe 102. When an instance of marking is triggered, the ports 120 will spray or otherwise discharge ink, or another skin-marking substance, onto the skin 106 to create a landmark 122. Although two ports 120 are shown in FIG. 1 for the probe 102, there may be more than two. As seen in FIG. 1, below the illustration of the probe 102, four marks 124 have been made by four respective ports 120. The landmark 122 may not consist of discrete marks 124; instead, it may be, for example, a circular single mark. Or it may simply be curved, depending of the probe face shape. The landmark 122 records a position 126 of the probe 102 at the instance of marking. Advantageously, the underlying, bony structure assures that the landmark 122, though contacted by the probe 102, fixes the position 126 with respect to structure within the brain that is the subject of imaging in what is proposed herein. This allows consistency in the time-sequential probe positioning for the purpose of monitoring lesion growth.

The instance of marking may be triggered by a user control 128, such as a depressible button, or it may triggered, without need for user intervention, automatically by the medical imaging device that features the probe 102. The device will typically include a display of the imaging dynamically acquired in the FOV 110. The live imaging changes dynamically, or in real time, as the field-of-view of the probe 102 changes by, for example, movement of the probe.

In the case of user triggering of the control 128 for marking, the user interactively depresses the button, when, in the course of the user manipulating the applied probe, a lesion of interest 112 appears on-screen. Acoustic aberration correction may be used to improve the imaging during the user's search for a lesion of interest 112. In one embodiment, the transducer array is able to move axially back and forth within the probe 102. The movement is done mechanically, as by a motor. A moving distance may be, for example, 0.25 millimeters (mm). The two acquisitions are combined to eliminate or reduce aberration caused by surface irregularities in the temporal bone 108. This is described in commonly-assigned U.S. Patent Publication No. 2012/0143058 to Powers et al., hereinafter "the Powers application", the entire disclosure of which is incorporated herein by reference. For live or real time imaging, the acquisition at one array displacement is interspersed or alternated with acquisition at the other displacement.

On the other hand, automatic triggering entails automatically and dynamically, in search of a lesion, recognizing a lesion from the interactive imaging. An example would be detecting a stationary blood pool in the brain.

Since liquid in the brain recovers less from forced displacement, acoustic radiation force (ARF) and A-mode displacement imaging can be used to detect areas of liquid. Also, the acoustic streaming velocity of blood, detectable by color Doppler or B-mode speckle tracking for example, serves as a signature to distinguish it from solid tissue. Using color Doppler to distinguish moving tissue from stationary objects is discussed in U.S. Pat. No. 5,487,387 to Trahey et al., and commonly-assigned U.S. Patent Publication No. 2010/0004540 to Thiele relates to speckle tracking of blood.

The FOV 110 is pre-set wide enough to include the one or more normal regions 114. The detected regions of liquid can be compared to an anatomic brain map to rule out ventricles, since solid regions are preferred in selecting the normal region(s) 114. The ultrasound device may issue ultrasound for measuring time-in-flight to the contralateral inner skull contour, for purposes of registering the anatomic brain map. Acoustic aberration correction may also be applied for this measurement.

However, alternatively or in addition, to further distinguish between stationary pools and naturally flowing blood in vessels, motion can be detected by Doppler techniques or speckle tracking.

Whether the triggering is automatic or manual, the landmark 122 records only the probe position 126. An orientation 130, 132 that, upon the marking, exists for the probe 102 performing the marking must also be reproducible. By reproducing the orientation 130, 132 and the position 126 for each sequential acquisition, a consistent acoustic window is obtained for evaluating a lesion identified in, or from, the initial application of the probe and tracking its growth or non-growth.

A central axis 134 of the probe 102 can be visualized as extending up out of a probe-skin center 126 so as to protrude out of the FIG. 1 drawing sheet. Two of the marks 124 can be imagined to reside on the x-axis, with the other two on the y-axis. Then, the central axis projects onto a plane of the x-axis that is normal to the y-axis at the first angle 130, and onto a plane of the y-axis that is normal to the x-axis at the second angle 132.

The orientation 130, 132 is with respect to the landmark 122.

If the patient is, for each acquisition, examined on a table equipped with fixed headgear, it is possible to obtain the orientation 130, 132 using electromagnetic sensors installed in the probe 102, as described in commonly-assigned U.S. Pat. No. 7,933,007 to Stanton et al. and U.S. Patent Publication 2010/0194879 to Pasveer et al.

However, an orientation reading is not needed. All that is needed is to ensure that the orientation 130, 132 with respect to the landmark 122 is kept consistent throughout the acquisitions for assessing lesion growth. The patient need not be confined to a fixed position. Instead, visual pattern matching methods, based dynamically on image acquisition by the probe 102, can be employed to match a current orientation to a reference orientation.

In the initial stage of lesion growth tracking, a lesion is located from the imaging, as described above. As also described above, the marking, upon location of a lesion, may be triggered by the user or may be automatically triggered. The imaging settings of the ultrasound device that exist upon marking are saved. In addition, B-mode imaging is used to save the imaging data within the current FOV 110.

In the case of automatic triggering, the normal region(s) 114 may, by means of the anatomic brain map, have already been selected upon the instance of marking. Ordinarily, in the case of user triggering, the normal region(s) are yet to be selected.

The identified lesion 112 and possibly already-identified normal region(s) 114 may, after the instance of marking, be subject to off-line processing. The saved B-mode imaging is viewed by a clinician. Precise boundaries may be ascribed, by the clinician, to the lesion 112, and to the normal region(s) 114, interactively with display of the saved imaging, as by moving a cursor on-screen. Thus, in the case of automatic triggering, the lesion boundaries assumed, and any normal region 114 boundaries assumed or selected, at that time are now made more precise or may be redrawn. Computed tomography (CT), which affords greater resolution than ultrasound for soft tissue, optionally can be utilized for both the lesion 112 and normal region(s) 114. The CT scan is registered to the ultrasound imaging in a known manner, and the boundaries of the lesion 112 and normal region(s) 114 are adjusted accordingly.

In one embodiment, the normal region(s) 114 almost span the entire FOV 110, i.e., up to the contralateral skull surface, excluding the lesion 112 and regions of fluid. Of the latter regions, ventricles can be discerned from an anatomical brain map, and naturally flowing fluids in vasculature can be detected, as discussed herein above. In the followup stage, to be discussed immediately below, the matching occurs with RF data from the relatively full, normal region(s) 114. Thus, RF data spans a current FOV 110 within the imaging subject 104, and determining whether the proximity criterion is met involves detecting a region of fluid and excluding the region from the image-based pattern matching.

The followup stage of lesion growth tracking is made up of each of the sequential acquisitions after the initial stage.

In the followup stage, the first task, for each acquisition, is to regain the same, or nearly same, position 126 and orientation 130, 132 of the probe 102 with respect to the landmark 122. The user applies the face of the probe 102 to the landmark 112 to regain the position 126. The probe 102 is then manipulated, e.g., manually. When the current orientation of the probe 102 matches the reference orientation, i.e., the orientation that existed upon marking in the initial stage, an on-target light-emitting diode (LED) ring panel 138 on the probe 102 emits green light. In some embodiments, this event is preceded by a near-target LED ring pannel 140 emitting yellow light, as described in more detail below. The ring panel 140 affords user guidance that interacts with user manipulation of the applied probe.

Once the orientations are matched, acquisition commences for identifying, in the acquired imaging, current physical structure or extents of the lesion 112. The results are compared to previous results obtained in the initial and/or followup stage. Acoustic aberration correction, as described further above, may be used throughout the process to correct imaging acquisition.

Figure 2:
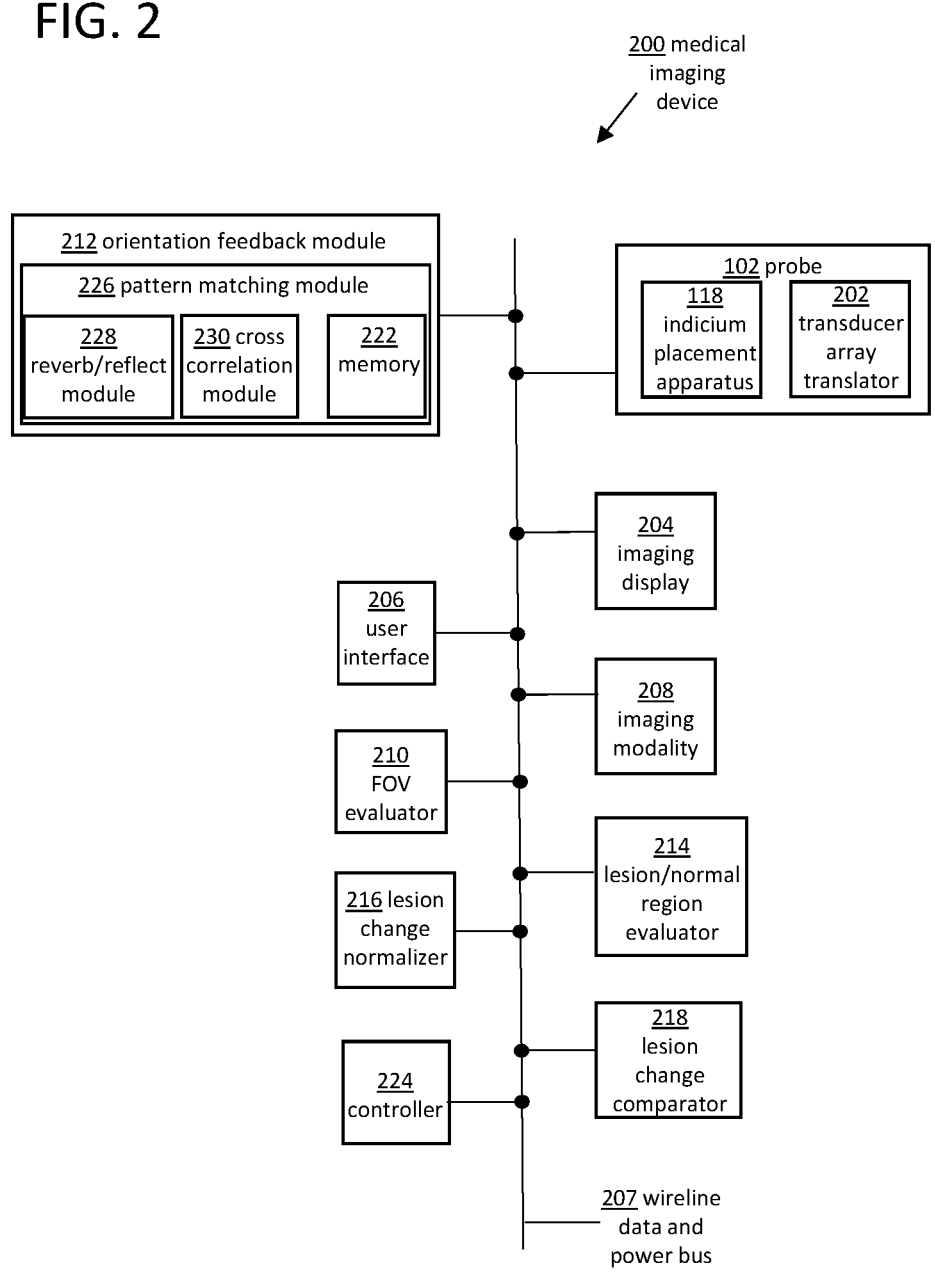
FIG. 2 is a functional diagram of the device of FIG. 1, in accordance with the present invention.

FIG. 2 shows, by way of illustrative and non-limitative example, a medical imaging device 200, which is discussed herein below in the context of ultrasound. The device 200 includes the probe 102, its indicium placement apparatus 118 and, optionally, a transducer array translator 202 for acoustic aberration correction as described herein above. The device 200 also includes an imaging display 204, a user interface 206, and various functional modules. The above components of the device 200 are communicatively connected, as by a wireline data and power bus 207. Among the imaging modalities 208 of the device 200 are B-mode; A-mode, for displacement imaging; and Doppler for streaming velocity measurement.

Although an ultrasound probe is discussed, other imaging technologies, such as infrared light and laser light for photoacoustic applications, are within the intended scope of what is proposed herein. The medical probe system of the '189 patent, which uses infrared light to interrogate a subject, can be modified with the intention of reproducing a result in accordance with the marking and the proximity criterion disclosed herein. All disclosure of the '189 patent is incorporated herein by reference in its entirety. Likewise, in the case of photoacoustic imaging, the medical imaging probe proposed herein can emit light, such as laser light, and use the responsive radiofrequency (RF) data in, for example, B-mode imaging pattern recognition for proximity determination. The innovative medical imaging probe described herein can accordingly either emit light to interrogate a subject, receive ultrasound in interrogating a subject, or both.

The functional modules include a quantitative field-of-view (FOV) evaluator 210, an orientation feedback module 212, a quantitative lesion/normal region evaluator 214, a lesion change normalizer 216, a lesion change comparator 218, a memory 222, and a controller 224. The orientation feedback module 212 comprises a pattern matching module 226 which, in turn, comprises a reverberation/reflection module 228, and an RF/image data cross-correlation module 230, and/or a sum absolute difference (SAD) module 232. The functional modules 210-232 and the rest of the device 200 may be implemented with any suitable and known combination of software, firmware and hardware. The controller 224 may be realized, for example, on a device having one or more integrated circuits, or as a suitably programmed computer readable medium.

Figure 3:
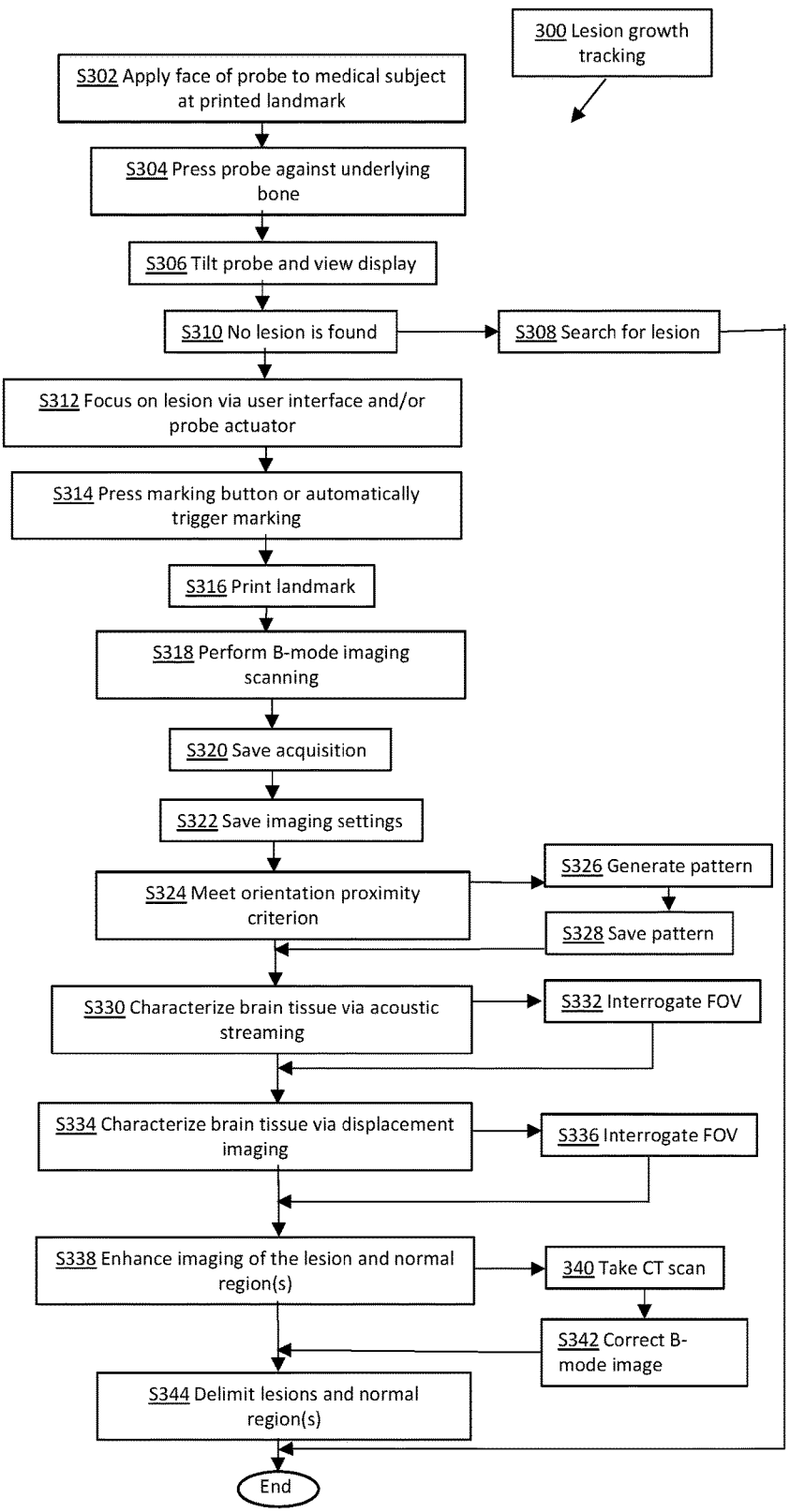
FIG. 3 is a flow diagram of an initial application of the probe of FIG. 1 to a medical subject, in accordance with the present invention.

FIG. 3 illustrates one example of an initial stage 300 of lesion growth tracking. The face of the probe 102 is applied to the skin 106 of the medical subject 104 at the printed landmark 122 (step S302). The probe face is pressed against the underlying bone 108 (step S304). The user tilts the probe 102 while viewing the display 204 (step S306). This continues in search of a lesion (step S308), but may end if no lesion is to be found (step S310).

If and when the user locates (step S308), from the display 204, a lesion of interest 112, the user may immediately press the marking button 128 to trigger marking (step S314). The user may also operate the user interface 206, or user actuator on the probe 102, to focus in to some extent on the lesion 112 (step S312) before pressing the marking button 128 (step S314), while still including the normal region(s) 114 for pattern matching in the followup stage. Alternatively, in the case of automatic triggering (S314), if a blood pool is detected (step S308), the automatic triggering may be accompanied by automatic focusing of the FOV 110 (step S312) prior to B-mode acquisition over the FOV in the initial stage.

Immediately responsive to pressing the marking button 128, or to automatic triggering/focusing, the landmark 122 is printed (step S316). In addition, B-mode imaging scanning is performed to span the current, perhaps adjusted, FOV 110 (step S318), and the acquisition is saved (step S320). The imaging settings are also saved (step S322). The B-mode imaging may, or may, not be subject to acoustic aberration correction.

If a reverberation/reflection pattern is to be used in meeting the orientation proximity criterion (step S324), the window on receive can be made very short. As seen from FIG. 1 of the Powers application, a Type I reverberation occurs between the probe surface and the skull of a patient, and is detectable within the very short time window on receive. The Type IIa reverberation is, given the very short time window, detectable as a reflection from the skull. Any subsequent reflection back from the brain is outside the time window and therefore not part of the reflection/reverberation pattern. The Type III reverberation shown on the left, which is likewise a reflection from bone, would also be detectable within the short window. If a single transducer element is fired, a Type IIa reflected signal may be incident upon the transducer array within the very short time window. A pattern of reflection from bone, e.g., the temporal bone 108, can be utilized. Likewise, the Type I and III reverberation signals mentioned herein above may provide a utilizable pattern. A pattern of both reflection, and reverberation, from bone is also utilizable. One or more pulses can be issued. They can be issued serially or concurrently, via a one- or two-dimensional array of transducers, the receive time window being kept very short (step S326). Acoustic aberration correction, if implemented for the device 200, is withheld or suppressed, since it is the aberration itself, due to the outer surface of the temporal bone 108 that gives the pattern its distinctive signature for the particular position 126 of the probe 102. As a beneficial aspect, the signature is much more unlikely than soft tissue to change over the time between imaging acquisitions in the lesion monitoring. The nature of the temporal bone, with its surface irregularities, therefore offers reliability in regaining the initial probe orientation that existing upon marking. The pattern generated (step S326) is saved (step S328) as a reference pattern of reflection, and/or reverberation, from bone. There is no effort made to image the normal region(s) 114 specifically in this type of pattern matching, since the very short receive window confined imaging to the surface of the temporal bone 108 or not much deeper than the temporal bone surface. In particular the imaging depth need not be more than bone deep, that bone, e.g., the temporal bone 108, being a bony structure that immediately underlies the probe 102 in the direction of propagation of the ultrasound beam. However, the normal region(s) 114 do serve their other function of providing a basis for lesion growth measurement normalization, and also the normalizing function in case other complementary image pattern matching is employed.

If acoustic streaming is to be used to characterize brain tissue (step S330), the entire FOV 110 may be interrogated (step S332). The probe 102 issues acoustic radiation force (ARF) to move tissue. Color Doppler, or speckle tracking for example, is used to measure the velocity of movement. The measured velocity can, for example, indicate that the moving tissue is blood. More generally, the measure velocity may be indicative of a particular physical structure. Measured velocities over a region within the brain can reveal the size or extent of a region having a particular physical structure, such as a blood pool, i.e., a type of lesion.

Alternatively or in addition, if displacement imaging is to be used to characterize brain tissue (step S334), A-mode displacement imaging is performed on brain tissue subjected to ARF. The entire FOV 110 may be interrogated (step S336). Fluids tend to continue to move under ARF; whereas, solid tissue recoils back to its original position. A push pulse can be preceded by a tracking pulse, for reference, and followed by a tracking pulse. A series of three or more pushes can be issued, and tissue displacement is tracked in the direction of push, i.e., in the direction of maximum displacement. Maximum displacement over the whole series, i.e., from the tracking pulse preceding the first push to the (last) tracking pulse following the last push, can be measured over a range of tissue depths from the probe 102. An envelope of the curve will distinguish, by virtue of its displacement magnitude, a region of solid tissue from a region of liquid tissue. A liquid region may be a blood pool if stationary, and, as mentioned herein above, Doppler and speckle tracking are two examples of techniques usable to detect motion. The medical imaging device 200 could optionally report to the user a message such as "BLOOD POOL DETECTED." The message can appear on the display 204 or as a rolling message in a panel on the probe 102.

Additional off-line processing may now occur at the end of the initial stage.

If computed tomography (CT) is to be performed to enhance the imaging of the lesion 112 and the normal region(s) 114 (step S338), a CT scan is taken (step S340). The saved ultrasound B-mode imaging is accordingly corrected based on the CT imaging (step S342).

In any event, the saved ultrasound B-mode imaging is optionally subject to display and scrutiny, by a clinician for example, to better identify and to, via the user interface 206, delimit lesions 112 and the normal region(s) 114 (step S344).

Figure 4:
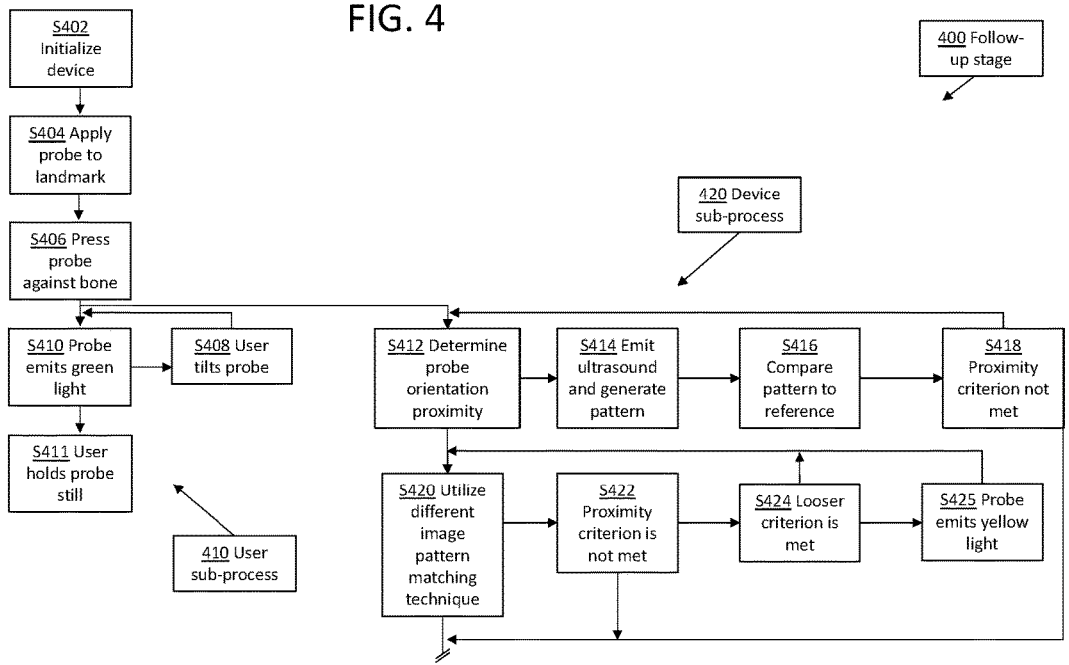
FIG. 4 is flow diagram of a subsequent application of the probe of FIG. 1 to the medical subject, in accordance with the present invention.
Figure 4:
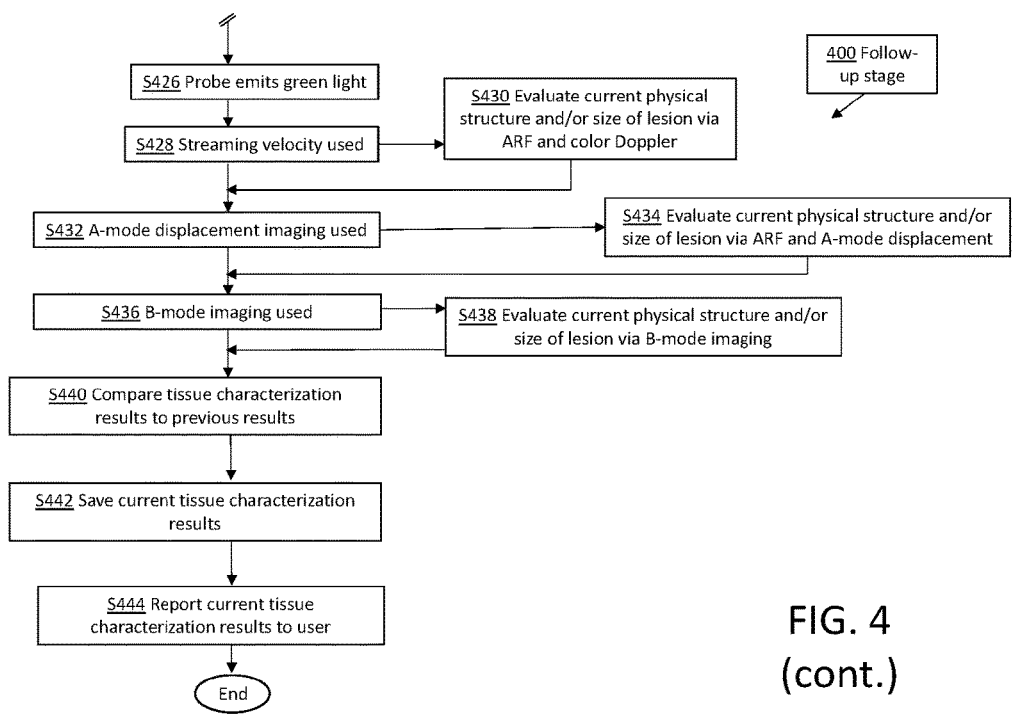

A followup stage 400 is exemplified by FIG. 4. The device 200 is initialized with the values saved in the above-indicated steps S320, S322, S328, S342, S344 (step S402).

In a user sub-process 410, the user applies the probe 102 to the landmark 122 (step S404). The probe face is pressed against the underlying bone 108 (step S406). The user tilts the probe 102 (step S408) until the on-target light-emitting diode (LED) ring panel 138 on the probe 102 emits green light (step S410). Before, the green light, the user may halt temporarily if the near-target LED ring pannel 140 emits yellow light. Once the green light appears (step S410), the user will hold the probe 102 still (S411).

Once step S406 is executed, a device sub-process 420 concurrent with the user sub-process 410 takes effect.

In accordance with the device sub-process 420, if reverberation/reflection pattern matching is to be used in determining probe orientation proximity (step S412), ultrasound is emitted to generate a current pattern (step S414). The pattern is compared to the corresponding stored pattern, or "reference pattern" from the initial stage (step S416). The pattern can be based on the received radiofrequency (RF) data, or image data such as that which is based on the received RF data. For example, the pattern can be based on the magnitude of the RF or image data over time and over space, i.e., among the various transducer elements. A proximity criterion for application to a comparison between the current pattern and a previous, i.e., reference, pattern may be based on a particular moment of time within the receive window. The current magnitude on each channel of a respective transducer element is compared, one-to-one, to the reference magnitude for that channel. The comparison involves taking the difference. These differences are summed to yield a similarity metric. Alternatively or in addition, a given delay pattern over the transducer elements can be found, in an iterative process for example that introduces different increments/decrements element-wise, to bring amplitudes in a reference pattern into near registration, within a predetermined threshold. The given delay pattern may, for example, add, element-by-element, different positive or negative delays, resulting in an augmented delay pattern that achieves registration. The similarity metric may then be based on the magnitude of delays of the given pattern, i.e., proximity of the augmented delay pattern to the reference delay pattern. Or, the similarity metric can be computed based on both delay and amplitude patterns. If, based on the similarity metric, a predetermined proximity criterion is not met (step S418), return is made to step S414. The criterion is therefore based on at least one of mutual proximity of patterns of delay over transducer elements and mutual proximity of patterns of amplitude over transducer elements. Alternatively, instead of returning to step S414 at this time, a looser criterion may be tried in order to see whether the near-target LED ring pannel 140 is to now emit yellow light; however, the irregularity of the bone surface may provide little or no warning prior to a match. However, other pattern matching techniques such as those discussed immediately below can concurrently be applied, as a supplement, to provide the warning in advance.

If, on the other hand, the reverberation/reflection pattern matching is not to be used (step S412), another image pattern matching technique is utilized (step S420). For example, RF data from the current B-mode imaging in the current FOV 110, or image data derived from the RF data, can be dynamically matched by cross-correlation to the respective reference RF or image data of the normal region(s) 114 of the acquisition that was saved in step S320 and was possibly enhanced in the off-line steps S342, S444 of the initial stage. An alternative to cross-correlation is the SAD algorithm, described, for instance, in commonly-assigned U.S. Pat. No. 6,299,579 to Peterson et al.

If the proximity criterion is not currently met (step S422), but a looser, predetermined criterion of closeness is met (step S424), the near-target LED ring pannel 140 emits yellow light (S425). The yellow light thus serves as a real-time indication of closeness in meeting the proximity criterion.

Then, whether or not the looser criterion is met (step S424), the pattern matching continues at step S420.

If and when the proximity criterion in any of the above techniques is met (steps S418, S422), the initial stage probe orientation, or a probe orientation close to it, has been regained. Thus, the "pre-identified lesion" which is the lesion identified prior to the determining that the criterion is met, i.e., identified in the initial stage, is within the current FOV 110. The on-target light-emitting diode (LED) ring panel 138 on the probe 102 accordingly now emits green light (S426), as a user notification. Ordinarily, either the user will, in response, hold the probe 102 still or move the probe slowly enough that the instantaneous imaging acquisition needed for detecting and measuring any change in growth of the specific, detected, pre-identified lesion 112 is taken. If the yellow light appears or the green light disappears, the user can move the probe 102 back to achieve the desired orientation evidenced by the green light, and hold the probe still, to ensure the integrity of the current acquisition.

If streaming velocity is to be used in the followup, i.e., current, stage (step S428), ARF and color Doppler are utilized to measure velocity in the pre-identified lesion 112 and the surrounding or nearby normal region(s) 114 in the currently acquired imaging data, to evaluate current physical structure and/or an extent or size of the pre-identified lesion (step S430).

If, alternatively or in addition, A-mode displacement imaging is to be used (step S432), ARF and A-mode displacement imaging are applied to the pre-identified lesion 112 and the surrounding or nearby normal region(s) 114 in the currently acquired imaging data, to evaluate current physical structure and/or an extent or size of the pre-identified lesion (step S434).

If, alternatively or in addition, B-mode imaging is to be used (step S436), it is used to evaluate size and/or physical structure of the pre-identified lesion 112 and the surrounding or nearby normal region(s) 114 in the currently acquired imaging data (step S438). For example, based on ultrasound image brightness, the extent of a blood pool is determined.

The above, current tissue characterization results of the followup stage, that may include a quantitative evaluation of the lesion 112, are compared to previous results, i.e., of at least one previous time point in the monitoring in the followup stage and/or the initial stage (step S440). Thus, the pre-identified lesion 112 is monitored specifically, and is monitored for change in the lesion, such as growth of the lesion.

The current tissue characterization results are saved (step S442) for future comparisons performable in step S440.

The current comparative results are reported to the user (step S444). Sample messages are: "BLOOD POOL CONTINUES TO GROW" and "BLOOD POOL GROWTH ACCELERATING." The reported results could include actual size measurements of a lesion, associated times of measurement, and a graph of the measurements. The messages can appear on the display 204 or as a rolling message in a panel on the probe 102.

A medical imaging probe for contact with an imaging subject includes an indicium placement apparatus for, while the probe is in contact, selectively performing an instance of marking the subject so as to record a position of the probe. The device may further include a feedback module for determining whether an orientation, with respect to a the mark, that currently exists for a medical imaging probe of the device meets a criterion of proximity to a predetermined orientation. Responsive to the determination that the criterion is met, a quantitative evaluation may be made automatically and without need for user intervention, via imaging via the probe, of a lesion that was, prior to the determination, specifically identified for the evaluation. Change, such as growth, in the lesion, like a brain lesion, may thereby be tracked over consistent sequential imaging acquisitions, such as through ultrasound.

Portable and economical, medical ultrasound is viably utilized in a point-of-care setting by clinicians trained or untrained in ultrasound usage. Advantageously, the temporal bone affords positional consistency for the probe and, by its surface irregularity, a reliable signature for probe orientation. Accordingly, consistent sequential imaging acquisitions are available in monitoring a specific lesion quantitatively for growth and change in physical structure.

While the invention has been illustrated and described in detail in the drawings and foregoing description, such illustration and description are to be considered illustrative or exemplary and not restrictive; the invention is not limited to the disclosed embodiments.

For example, the underlying bony structure need not be part of the skull, but can, for example, comprise a rib during a cardiovascular application.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A medical imaging device comprising:
   a medical imaging probe configured for contact with an imaging subject and for obtaining a plurality of images of the imaging subject, said medical imaging probe comprising: an indicium placement apparatus comprising at least one discharge port configured for, while said medical imaging probe is in contact with said imaging subject, selectively performing an instance of marking said imaging subject by discharging a skin-marking substance on the imaging subject so as to record a position of said medical imaging probe;
   a feedback module comprising a computer readable medium having executable instructions configured for determining whether an orientation, with respect to a mark resulting from said performing, that currently exists for the medical imaging probe meets a criterion of proximity to a predetermined orientation wherein said criterion is based on proximity of a current pattern of reflection from a temporal bone, reverberation from the temporal bone, or both reverberation and reflection from the temporal bone correspondingly to a saved reference pattern of reflection from the temporal bone, reverberation from the temporal bone, or both reverberation and reflection from the temporal bone obtained by the medical imaging probe at the position marked by the indicium placement apparatus;
   a comparative module comprising a computer readable medium having executable instructions configured for comparing a first image obtained at the predetermined orientation and a second image obtained at the orientation that satisfied the criterion, and identifying a clinical condition of an object present in at least one of the first and second images based on the comparison; and
   a display configured to present the identified clinical condition to a user.

2. The device of claim 1, wherein said predetermined orientation is an orientation, with respect to said mark, that existed for said medical imaging probe performing said marking upon said imaging subject.

3. The device of claim 1, wherein said mark is adapted to provide a landmark on said subject, wherein said feedback module, by said determining that said criterion is met, is further configured to determine that a current position of said medical imaging probe matches said landmark.

4. The device of claim 1, wherein the indicium placement apparatus is further configured for, automatically and without need for user intervention, performing said instance of marking in response to a detection of a lesion via displacement imaging of said imaging subject performed by the medical imaging probe, said device further configured such that a field of view of said medical imaging probe whose orientation is subject to said determining will, upon said determining that said criterion is met, include said lesion.

5. The device of claim 1, wherein said determining comprises pattern matching of the current pattern to the saved reference pattern based on image, or radiofrequency, data currently being acquired via said medical imaging probe.

6. The device of claim 5, wherein said data spans a current field of view within said imaging subject, said determining comprising detecting a region of fluid from the data and excluding, from said matching, said region of fluid.

7. The device of claim 1, wherein said criterion is based on at least one of mutual proximity of patterns of delay over transducer elements of the medical imaging probe and mutual proximity of patterns of amplitude over the transducer elements.

8. The device of claim 1, wherein said module is further configured with a user indicator configured for providing an indication of closeness in the meeting of said criterion while the medical imaging probe remains in contact with the imaging subject.

9. The device of claim 1, wherein the object comprises normal tissue or a lesion.

10. The device of claim 9, said lesion comprising a brain lesion.

11. The device of claim 1, wherein the comparing step comprises determining a size of said object, physical structure of said object, or both in said first and second images.

12. The device of claim 11, wherein a change of the size, physical structure or both of the object between the first and second images is indicative of the clinical condition.

13. The medical imaging device of claim 1, said device further comprising an indicator on the medical imaging probe configured for, after the clinical condition of said imaging subject has been identified and while a medical imaging probe is applied to the marked position, affording user guidance that interacts with user manipulation of the applied medical imaging probe and for, automatically and without need for further user intervention, monitoring, via imaging via said applied medical imaging probe, said object and for change in said object.

* * * * *